United States Patent [19]

Biedermann et al.

[11] 4,303,673

[45] Dec. 1, 1981

[54] N-PROPIONYLSARCOSINEANILIDES, PROCESS FOR THEIR PREPARATION, AND PHARMACEUTICAL COMPOSITIONS CONTAINING THEM

[75] Inventors: Jürgen Biedermann, Pulheim-Stommeln; Armin Wendel, Cologne; Hans Betzing, Horrem; Volker Neuser, Bergheim-Ahe, all of Fed. Rep. of Germany

[73] Assignee: A. Nattermann & Cie. GmbH, Cologne, Fed. Rep. of Germany

[21] Appl. No.: 184,309

[22] Filed: Sep. 5, 1980

[30] Foreign Application Priority Data

Sep. 18, 1979 [DE] Fed. Rep. of Germany ....... 2937698

[51] Int. Cl.³ .................. A61K 31/165; A61K 31/40; A61K 31/24; C07C 103/20
[52] U.S. Cl. ............................. 424/324; 260/326.47; 424/274; 424/309; 560/16; 564/79; 564/99; 564/154; 564/155; 564/157; 564/158
[58] Field of Search ............... 564/154, 155, 157, 158, 564/79, 99; 560/16; 260/326.47; 424/309, 274, 327

[56] References Cited

U.S. PATENT DOCUMENTS

| | | | |
|---|---|---|---|
| 2,447,587 | 8/1948 | Martin et al. | 564/155 X |
| 3,382,243 | 5/1968 | Bell et al. | 564/155 X |
| 3,657,341 | 4/1972 | Thorne | 564/155 |
| 3,707,559 | 12/1972 | Mazur et al. | 564/155 |
| 4,058,523 | 11/1977 | Mori et al. | 564/153 X |

Primary Examiner—John Doll
Attorney, Agent, or Firm—Burns, Doane, Swecker & Mathis

[57] ABSTRACT

The invention provides N-propionylsarcosineanilides of the formula:

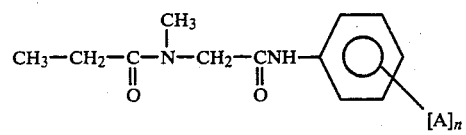

wherein n is an integer of 1 to about 3 and the substituent A which can be the same or different when n is greater than 1 is selected from the group consisting of trifluoromethyl; halogen; nitro; acetyl; a straight-chain or branched alkyl group having 1 to 4 carbon atoms; a straight-chain or branched alkoxy group having 1 to 4 carbon atoms; a straight-chain or branched alkylmercapto group having 1 to 7 carbon atoms; a substituted alkylmercapto group of the formula:

$$-S-(CH_2)_n-\underset{R_1}{CH}-R_2 \qquad II$$

wherein n is an integer of 1 or 2, $R_1$ can represent hydrogen and methyl, and $R_2$ can represent hydroxyl, and an amino group of the formula:

$$-NR_6R_7 \qquad V$$

wherein $R_6$ can represent hydrogen, and methyl, and $R_7$ can represent methyl, substituted benzyl, and $R_6$ and $R_7$, together with the nitrogen, can constitute a substituted pyrrolidine ring; a sulphonyl group of the formula:

$$-SO_2R_3 \qquad III$$

wherein $R_3$ can represent amino, and alkyl of 1 to 3 carbon atoms; or an aminoethoxycarbonyl group of the formula:

$$-COO(CH_2)_2-N\underset{R_5}{\overset{R_4}{\diagup}} \qquad IV$$

wherein $R_4$ and $R_5$ which can be the same or different can represent hydrogen, methyl, and ethyl; and the pharmaceutically acceptable salts thereof. These compounds may be made from N-propionylsarcosine and the corresponding substituted anilines. They have central vaso-active properties, are useful in controlling metabolism, inhibit the aggregation of thrombocytes, can be used for the treatment of the cerebroischaemic and atrophic type, and have tranquillizing properties.

9 Claims, No Drawings

N-PROPIONYLSARCOSINEANILIDES, PROCESS FOR THEIR PREPARATION, AND PHARMACEUTICAL COMPOSITIONS CONTAINING THEM

DESCRIPTION

The present invention relates to N-propionylsarcosineanilides which have interesting pharmacodynamic properties, their preparation and pharmaceutical compositions containing them.

The N-propionylsarcosineanilides of the present invention may be represented by the structural formula:

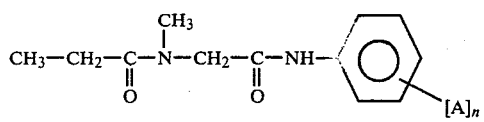   I wherein n is an integer which can vary from 1 to about 3, and the substituent A which can be the same or different when n is greater than 1 is selected from the group consisting of trifluoromethyl; halogen; nitro; acetyl; a straight-chain or branched alkyl group having 1 to about 4 carbon atoms; a straight-chain or branched alkoxy group having 1 to about 4 carbon atoms; a straight-chain or branched alkylmercapto group having 1 to about 7 carbon atoms; a substituted alkylmercapto group of the formula:

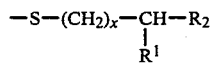   II wherein x is the integer 1 or 2, $R_1$ represents hydrogen or methyl and $R_2$ represents —OH or an amino group of the formula:

—$NR_6R_7$   V wherein $R_6$ represents hydrogen or methyl and $R_7$ denotes methyl or optionally substituted benzyl, or $R_6$ and $R_7$, together with the nitrogen, constitute a substituted pyrrolidine ring, such as, for example, 2-oxopyrrolidine; a sulphonyl group of the formula:

—$SO_2R_3$   III wherein $R_3$ is —$NH_2$ or alkyl of 1 to 3 carbon atoms; or an aminoethoxycarbonyl group of the formula:

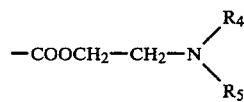   IV wherein $R_4$ and $R_5$ which may be the same or different each can represent hydrogen, methyl or ethyl. Pharmaceutically acceptable salts of the aforedescribed compounds are also within the scope of the present invention.

Examples of straight-chain or branched alkyl groups of 1 to 4 carbon atoms include methyl, ethyl, propyl, isopropyl, and n-butyl. Examples of alkoxy groups having 1 to 4 carbon atoms include methoxy and isopropoxy.

Examples of straight-chain or branched alkylmercapto groups having 1 to 7 carbon atoms include methylmercapto, n-propylmercapto, isopropylmercapto, sec.-butylmercapto, and n-heptylmercapto.

Examples of substituted alkylmercapto groups of the formula II include 2-hydroxypropylmercapto, 3-(dimethylamino)-propylmercapto, 2-(N-methyl-N-benzylamino)-ethylmercapto, 2-(N-methyl-N-(3,4-dimethoxybenzyl)-amino)-ethylmercapto, and 2-(2-oxopyrrolildin-1-yl)-ethylmercapto.

Examples of sulphonyl groups of the formula III include aminosulphonyl and isopropylsulphonyl. An example of an aminoethoxycarbonyl group of the formula IV is 2-(diethylamino)-ethoxycarbonyl.

Preferably A represents methyl, ethyl, isopropyl, methylmercapto, ethylmercapto, isopropylmercapto, or chloro radicals in the 4-, 2,6-, or 2,4,6-positions of the phenyl ring.

The invention also provides a process for the preparation of the compounds of formula I which comprises reacting N-propionylsarcosine of the formula:

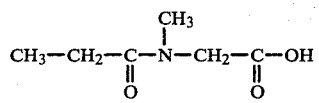   VI with an amine of the formula:

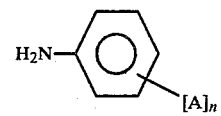   VII in which A and n are as defined above, in the presence of N,N'-dicyclohexylcarbodiimide and organic solvent, such as chloroform, methylene chloride, tetrahydrofuran, acetonitrile or ethyl acetate, and preferably at a temperature between 0° C. and the boiling point of the particular solvent.

The customary preparative processes for amides, such as, for example, the process via mixed anhydrides using chloroformic acid esters, and also the use of activated esters of N-propionylsarcosine, such as, for example, nitrophenyl esters, cyanomethyl esters or trichlorophenyl esters, or the use of N-propionylsarcosine chloride are also suitable for obtaining the compounds of the invention.

The following anilines are examples of suitable starting compounds of the formula VII: p-methylaniline, p-ethylaniline, p-propylaniline, p-butylaniline, p-(1-methylpropyl)-aniline, p-isopropylaniline, o-methylaniline, 2,4-dimethylaniline, 3,4-dimethylaniline, 2,3-dimethylaniline, 2,6-dimethylaniline, 2,4,6-trimethylaniline, p-methoxyaniline, 3,4-dimethoxyaniline, 2,5-dimethoxyaniline, 3,4,5-trimethoxyaniline, 2,6-diethylaniline, 2-methyl-4-methoxy-aniline, 2-methoxy-5-methyl-aniline, 2-methoxy-5-chloro-aniline, 2-methyl-5-fluoro-aniline, 2-methyl-5-chloro-aniline, 2-methyl-4-chloro-aniline, 2-methyl-6-chloro-aniline, 2-trifluoromethyl-aniline, 4-isopropoxyaniline, 4-[2-(N,N-diethylamino)-ethoxycarbonyl]-aniline, 3-chloro-4,6-dimethyl-aniline, 3-acetylaniline, 3-nitroaniline, 3-methylmercaptoaniline, 4-acetylaniline, 4-methylmercaptoaniline, 4-ethylmercaptoaniline, 4-isopropylmercaptoaniline, 4-(2-butylmercapto)-aniline, 4-[2-(N-benzyl-N-methylamino)-ethylmercapto]-aniline, 4-[2-(N-(3,4-dimethoxyphenylmethyl)-N-methylamino)-ethylmercapto]-aniline, 4-[2-

(N,N-dimethylamino)-ethylmercapto]-aniline, 4-isopropylsulphonylaniline, 4-aminosulphonylaniline, 2-isopropylmercaptoaniline, 4-heptylmercaptoaniline, 2,6-dichloroaniline, 2,6-difluoroaniline, and 4-[2-(2-oxopyrrolidin-1-yl)-ethylmercapto]aniline.

N-Propionylsarcosine is obtained by acylating sarcosine with propionic anhydride analogously to the process for the preparation of acetylglycine by the method of R. M. HERBST and D. SHEMIN, Organic Synthesis 19 (1939), 4.

The compounds of the invention possess valuable pharmacological properties. Such compounds display central vaso-active properties, can be used to control metabolism, and they also inhibit the aggregation of thrombocytes and are suitable for the treatment of diseases of the cerebroischaemic and atrophic type, including those of the organic psychosyndrome and migraine. In addition, the new compounds display good tranquillizing properties.

The new compounds can be converted in known manner into pharmaceutical compositions such as tablets, capsules, dragees, pills, emulsions, suspensions and solutions, using pharmaceutically suitable diluents or excipients.

The following may be mentioned as examples of such auxiliaries: non-toxic, organic solvents, such as vegetable oils (for example groundnut oil or soya oil), alcohols (for example groundnut oil or soya oil), alcohols (for example polyethylene glycol or glycerol), solid excipients, such as, for example, ground minerals (kaolin, talc or silicates), sugars (for example lactose or glucose), emulsifiers (for example fatty acid esters or fatty alcohol ethers), dispersing agents (for example methylcellulose of starch), and lubricants (for example talc, stearic acid or cocoa butter). Administration is customarily effected enterally, using doses of 1–1,000 mg, preferably 10–100 mg. or parenterally, using doses of 0.1–100 mg, especially 1–20 mg.

The preparation of the new N-propionylsarcosine-anilides is illustrated in greater detail by means of the following examples:

EXAMPLE 1

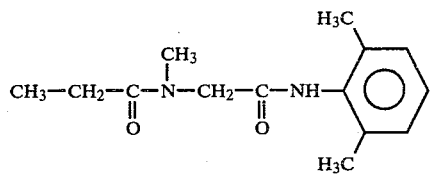

$N_\alpha$-Propionylsarcosine-2,6-dimethylanilide.

24.7 g (0.17 mol) of N-propionylsarcosine $C_6H_{11}NO_3$ [145.2] (melting point of 75° C., prepared from sarcosine and propionic anhydride analogously to the process for the preparation of acetylglycine by the method of R. M. HERBST and D. SHEMIN, Organic Synthesis 19 (1939), 4) and 20.6 g (0.17 mol) of 2,6-dimethyl-aniline $C_8H_{11}N$ [121.2] are dissolved in 160 ml of tetrahydrofuran, the solution is cooled to an internal temperature of approx. +4° C. in an ice/water bath and a solution of 35.1 g (0.17 mol) of N,N'-dicyclohexylcarbodiimide $C_{13}H_{22}N_2$ [206.3] in 50 ml of tetrahydrofuran is added. Stirring is continued for a further 6 hours at room temperature, the precipitated N,N'-dicyclohexylurea is filtered off and the filtrate is concentrated in vacuo. The residue is dissolved in ethyl acetate and the mixture is filtered through active charcoal and a large quantity of ether is added to the filtrate. The crude product precipitated is filtered off from the mixture of solvents and recrystallized from hot water. Yield: 27.6 g (65.4% of theory) $C_{14}H_{20}N_2O_2$ [248.3]. Melting point: 128°–130° C.

Thin layer chromatography: Prepared thin layer chromatographic plates of silica gel 60 $F_{254}$(Merck). Spraying reagent: Bromocresol Green (0.5% strength, Merck)

$R_f$=0.74; Eluant St: 65:25:4 (V/V/V) chloroform/methanol/water $R_f$=0.78; Eluant Y: 70:26:4 (V/V/V) chloroform/methanol/25% ammonia.

The identity of the compound obtained with the structure indicated is confirmed by IR, $^1$H-NMR and mass spectrograms.

EXAMPLE 2

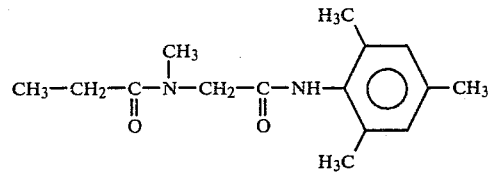

$N_\alpha$-Propionylsarcosine-2,4,6-trimethylanilide.

A solution of 24.8 g (0.12 mol) of N,N'-dicyclo-hexylcarbodiimide $C_{13}H_{22}N_2$ [206.3] in 30 ml of tetrahydrofuran (THF) is added to 17.4 g (0.12 mol) of N-propionylsarcosine $C_6H_{11}NO_3$ [145.2] and 16.2 g (0.12 mol) of 2,4,6-trimethylaniline $C_9H_{13}N$ [135.2] in 100 ml of THF at an internal temperature of 4° C., while stirring, and the mixture is then stirred for a further 6 hours at room temperature. After the precipitated N,N'-dicyclohexylurea has been filtered off, the resulting solution is concentrated in vacuo, the residue is dissolved in ethyl acetate and the solution filtered through active charcoal and ether is added to the filtrate. The crude product precipitated is filtered off and recrystallized from hot water. Yield: 16.2 g (51.4% of theory) $C_{15}H_{22}N_2O_2$ [262.4] Melting point: 159°–160° C.

The identity of the compound obtained with the structure indicated is confirmed by IR, $^1$H-NMR and mass spectrograms.

Thin layer chromatography (see under Example 1 for explanation): $R_f$=0.84 (eluant St); $R_f$=0.84 (eluant Y).

EXAMPLE 3

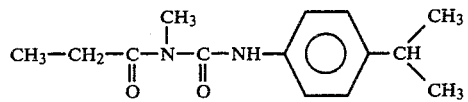

$N_\alpha$-Propionylsarcosine-4-isopropylanilide.

A solution of 28.9 g (0.14 mol) of N,N'-dicyclo-hexylcarbodiimide $C_{13}H_{22}N_2$ [206.3] in 40 ml of absolute chloroform is added, while stirring, to 20.3 g (0.14 mol) of N-propionylsarcosine $C_6H_{11}NO_3$ [145.2] and 18.9 g (0.14 mol) of 4-isopropylaniline $C_9H_{13}N$ [135.2] in 120 ml of absolute chloroform, at an internal temperature of 4° C. (ice/water bath). The contents of the flask are stirred for a further 6 hours at room temperature. The precipitated N,N'-dicyclohexylurea is then filtered off from the liquid phase and the latter is concentrated in vacuo. The residue is dissolved in ethyl acetate, the solution is filtered through active charcoal and the filtrate is concentrated to dryness. The crude product is suspended in ether, thoroughly stirred and filtered off. The residual solid is dissolved in methanol, the mixture is again filtered through active charcoal, the filtrate is concentrated and the residue is again stirred thoroughly with ether. The end product, which is now clean, is filtered off and dried to constant weight in vacuo. Yield: 14.3 g (38% of theory) $C_{15}H_{22}N_2O_2$ [262.4] Melting point: 117°–118° C.

The identity of the resulting compound with the structure indicated is confirmed by IR, $^1$H-NMR and mass spectrograms.

Thin layer chromatography (see under Example 1 for explanation): $R_f$=0.84 (eluant St); $R_f$=0.86 (eluant Y).

EXAMPLE 4

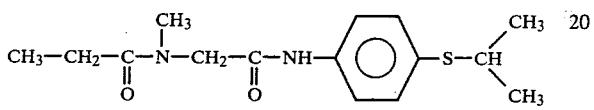

$N_\alpha$-Propionylsarcosine-4-isopropylmercaptoanilide.

14.5 g (0.1 mol) of N-propionylsarcosine $C_6H_{11}NO_3$ [145.2] and 16.7 g (0.1 mol) of 4-isopropylmercaptoaniline $C_9H_{13}NS$ [167.3] in 100 ml of absolute chloroform are heated to the boil for 3 hours, while stirring, under a reflux condenser, together with 20.6 g (0.1 mol) of N,N'-dicyclohexylcarbodiimide. After cooling, the precipitated N,N'-dicyclohexylurea is filtered off, the chloroform solution is concentrated and the residue is taken up in ethyl acetate. This solution is filtered through active charcoal and the filtrate is concentrated in vacuo. The residual solid substance is thoroughly stirred with ether, filtered off and dried. Yield: 16.2 g (55.0% of theory) $C_{15}H_{22}N_2O_2S$ [294.4] Melting point: 92° C.

The identity of the resulting compound with the structure indicated is confirmed by IR, $^1$H-NMR and mass spectrograms.

Thin layer chromatography (see under Example 1 for explanation): $R_f$=0.76 (eluant St); $R_f$=0.84 (eluant Y)

EXAMPLE 5

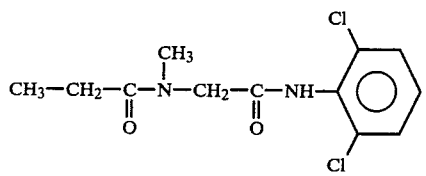

$N_\alpha$-Propionylsarcosine-2,6-dichloroanilide.

A solution of 22.7 g (0.11 mol) of N,N'-dicyclo-hexylcarbodiimide $C_{13}H_{22}N_2$ [206.3] in 30 ml of tetrahydrofuran (THF) is added to 16.0 g (0.11 mol) of N-propionylsarcosine $C_6H_{11}NO_3$ [145.2] (see under Example 1 for preparation) and 17.8 g (0.11 mol) of 2,6-dichloroaniline $C_6H_5Cl_2N$ [162] in 100 ml of THF at an internal temperature of 4° C. (ice/water bath), while stirring, and the mixture is stirred for a further 4 hours at room temperature and finally for 0.5 hour at the boil.

The precipitated N,N'-dicyclohexylurea is filtered off, the filtrate is concentrated in vacuo, the residue is dissolved in ethyl acetate and the solution is filtered through active charcoal. The filtrate is concentrated again and the oily residue is dissolved in ether and stirred. The desired product begins to crystallize out after approx. 2 hours. The crude product is filtered off and recrystallized from ethyl acetate (diisopropyl ether). Yield: 14.3 g (44.9% of theory) $C_{12}H_{14}Cl_2N_2O_2$ [289.2] Melting point: 122° C.

The identity of the resulting compound with the structure indicated is confirmed by IR, $^1$H-NMR and mass spectrograms.

Thin layer chromatography (see under Example 1 for explanation): $R_f$=0.76 (eluant St); $R_f$=0.80 (eluant Y).

What is claimed is:

1. N-Propionylsarcosineanilides of the formula:

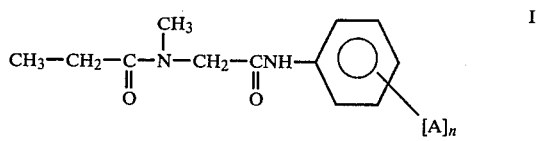

wherein n is an integer which can vary from 1 to about 3 and the substituent A which can be the same or different when n is greater than 1 is selected from the group consisting of trifluoromethyl; halogen; nitro; acetyl; a straight-chain or branched alkyl group having 1 to about 4 carbon atoms; a straight-chain or branched alkoxy group having 1 to about 4 carbon atoms; a straight-chain or branched alkylmercapto group having 1 to about 7 carbon atoms; a substituted alkylmercapto group of the formula:

wherein x is the integer 1 or 2, $R_1$ can represent hydrogen and methyl, and $R_2$ can represent hydroxyl and an amino group of the formula:

wherein $R_6$ can represent hydrogen, and methyl, $R_7$ can represent methyl, substituted benzyl, and $R_6$ and $R_7$ together with the nitrogen can constitute a substituted pyrrolidine ring; a sulphonyl group of the formula:

wherein $R_3$ can represent amino, alkyl of 1 to 3 carbon atoms; and an aminoethoxycarbonyl group of the formula:

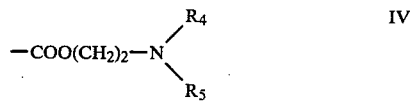

wherein $R_4$ and $R_5$ which can be the same or different can represent hydrogen, methyl and ethyl; and the pharmaceutically acceptable salts of said compounds.

2. N-Propionylsarcosineanilides represented by formula I in claim 1 in which A is selected from the group consisting of methyl, ethyl, isopropyl, methylmercapto, ethylmercapto, isopropylmercapto, or chloro radicals, said radicals being in the 4-, 2,6-, or 2,4,6-positions of the phenyl ring in formula 1.

3. $N_\alpha$-Propionylsarcosine-2,6-dimethylanilide.

4. $N_\alpha$-Propionylsarcosine-2,4,6-trimethylanilide.

5. N$_\alpha$-Propionylsarcosine-4-isopropylanilide.

6. N$_\alpha$-Propionylsarcosine-4-isopropylmercaptoanilide.

7. N$_\alpha$-Propionylsarcosine-2,6-dichloroanilide.

8. The compounds of claim 1 wherein the substituent A is selected from the group consisting of halogen, a straight or branched alkyl group having 1 to about 4 carbon atoms; and a straight-chain or branched alkylmercapto group having 1 to about 7 carbon atoms.

9. A pharmaceutical composition comprising an effective tranquilizing amount of an N-propionylsarcosine-analide as claimed in any one of claims 1 to 7 and at least one compatible pharmaceutical diluent or excipient.

* * * * *